United States Patent [19]

Klainer et al.

[11] Patent Number: 5,165,005
[45] Date of Patent: * Nov. 17, 1992

[54] PLANAR AND OTHER WAVEGUIDE REFRACTIVE INDEX SENSORS USING METAL CLADDING

[75] Inventors: Stanley M. Klainer; Marcus S. Butler, both of Henderson, Nev.

[73] Assignee: FiberChem Inc., Las Vegas, Nev.

[*] Notice: The portion of the term of this patent subsequent to Jun. 25, 1908 has been disclaimed.

[21] Appl. No.: 646,148

[22] Filed: Jan. 24, 1991

Related U.S. Application Data

[63] Continuation-in-part of Ser. No. 501,144, Mar. 31, 1990, Pat. No. 5,026,139, which is a continuation-in-part of Ser. No. 150,197, Jan. 29, 1988, Pat. No. 4,929,049.

[51] Int. Cl.$^5$ .............................................. G02B 6/02
[52] U.S. Cl. .................................. 385/129; 385/123; 385/141; 385/12; 356/128
[58] Field of Search ................ 350/96.29; 356/128, 356/133; 385/129, 123, 130, 141, 12

[56] References Cited

U.S. PATENT DOCUMENTS 4,929,049 5/1990 LeGoullon et al. ............ 350/96.29
5,026,139 6/1991 Klainer et al. ................. 350/96.29

FOREIGN PATENT DOCUMENTS 867149 12/1986 World Int. Prop. O. .

Primary Examiner—John D. Lee
Assistant Examiner—Stephen W. Barns
Attorney, Agent, or Firm—Henry P. Sartorio

[57] ABSTRACT

A species-specific metal clad segment on a waveguide, including a planar waveguide, allows controlled light leakage of light propagating through the waveguide by total internal reflection, to measure refractive index and identify chemical species. A waveguide sensor is designed for a particular chemical species by selecting a metal clad with an affinity for the species and by matching the refractive indices of the waveguide body, clad, metal clad segment and chemical species. Dual or multiple measurement methods use a pair or multiple metal clad segments of different specificity. The metal clad segment may include another material to provide a suitable refractive index while having the desired affinity for the chemical species or to provide a catalyst to react the species to form a reaction product which is more readily detected.

44 Claims, 5 Drawing Sheets

PLANAR AND OTHER WAVEGUIDE REFRACTIVE INDEX SENSORS USING METAL CLADDING

RELATED APPLICATIONS

This application is a CIP of Ser. No. 07/501,144 filed Mar. 31, 1990, now U.S. Pat. No. 5,026,139 issued June 25, 1991 which is a CIP of Ser. No. 07/150,197, filed Jan. 29, 1988, now U.S. Pat. No. 4,929,049 issued May. 29, 1990.

BACKGROUND OF THE INVENTION

The invention relates generally to chemical sensors using optical waveguides and more particularly to refractive index type chemical sensors using optical waveguides.

Optical waveguides, structures which guide light by total internal reflection, having been used in chemical sensors. Most waveguide chemical sensors are fiber optic chemical sensors (FOCS) based on optical fibers which guide light through the core by total internal reflection at the core/clad interfacing using a clad of lower refractive index than the core.

U.S. Pat. No. 4,929,049 describes a fiber optical refractive index sensor using a thin film metal clad which allow modulation of transmitted signal by changes in the refractive index of the surrounding medium. C.I.P. application Ser. No. 07/501,144, now U.S. Pat. No. 5,026,139, expands the concept to include selection of thin film metal clads which are specific to analytes of interest and to use combinations of different clad materials of different specificities to determine particular analytes.

U.S. Pat. No. 4,913,519 to Klainer, etal, describes an optical sensor for detection of ice formation or other chemical species in which a striped clad is formed on a fiber optic core or other waveguide structure. The speed stripes of clad material have a refractive index less than the light guiding means and substantially equal to the refractive index of the chemical species to be detected. When the species in not present, the gaps between the clad stripes allow light leakage so that little or no light is transmitted through the waveguide. When the species is present, it fills the gaps to form a complete clad which totally internally reflects light within the waveguide so that light is transmitted therethrough.

P.C.T. patent application PCT/CH86/00072 to Tiefenthaler, et al describes an optical waveguide sensor to selectively determine the presence of substances and the variations of refractive index in measured substances. The sensor is formed of a planar waveguide film, or a narrow strip, with a diffraction grating formed thereon. The thin film waveguide is formed of an oxide or polymer. The grating provides input or output coupling or acts as a Bragg reflector within the waveguide. The sample interacts with the waveguides in the region around the grating. In order to selectively establish the presence of specific substances, a layer of selective chemisorption material is formed on the thin film waveguides. The remainder of the waveguide surface may be covered by a low-index protective layer. According to Tiefenthaler the presence of a chemisorbed layer and/or the modification of the refractive index of the measurement substance modifies the refractive index within the waveguide film, which produces measurable changes in the propagation of light waves therein.

The metal clad FOCS of application Ser. No. 07/501,144, now U.S. Pat. No. 5,026,139 are advantageous for detecting a wide variety of chemical species; however, a disadvantage of the FOCS configuration is the small surface area available and the difficulty in attaching some clad materials to the fiber optic surface. It would be highly advantageous to apply the principles of the metal clad FOCS sensors to a planar waveguide of the type shown by Tiefenthaler. The larger surface area of the planar waveguide makes it much easier to apply the desired coatings, particularly where clad materials of specific crystallographic orientation are utilized. The improved coatings provide a sensor which can operate at high temperature with a long lifetime which is highly desirable for in-situ long-term monitoring applications. The ability to form patterned planar coatings also facilitates the production of waveguide sensors which use combinations of clad materials of different specificities to detect a chemical species of interest.

SUMMARY OF THE INVENTION

Accordingly, it is an object of the invention to provide a waveguide sensor which is sensitive to refractive index of a sample.

It is also an object of the invention to provide a waveguide sensor which is specific to various chemical species on the basis of refractive index.

It is another object of the invention to provide a waveguide sensor using thin film metal clads.

It is a further object of the invention to provide a waveguide sensor with multiple species-specific clad segments.

It is also an object of the invention to provide a refractive index based waveguide sensor which uses planar waveguides. The waveguide sensor is formed or a planar waveguide body having a conventional clad of lower refractive index formed on a surface thereof to provide total internal reflection of light within the waveguide. A portion of the conventional clad is replaced by at least one species-specific clad segment which produces controlled leakage of light as a function of the refractive index of the surrounding medium. The species-specific clad segments are thus only partly but not totally transmissive to light. The species-specific clad segment is designed to produce a localized refractive index at the interface with the waveguide body when the clad segment contacts a surrounding medium; this localized index is greater than that of the waveguide body so light can leak from the waveguide. The interaction of the sample with the waveguide through the specific clad segment thus modulates the transmission of light through the waveguide as a function of the refractive index of the medium. The changing refractive index of the medium (liquid or vapor or water emulsion) which contacts the clad changes the transmission characteristics of the waveguide which results in a signal (light intensity) change at the detector. The clad segment is of a thickness and is sufficiently light porous or light transmissive such that the leakage of light through the clad is modulated as a function of the refractive index of the surrounding medium which may be in liquid or vapor (gas) state. The species-specific clad segments may be thin film metal clad selected from Pt, Au, Rh, Rd, Ti, Zr, Hf, V, Nv, Ta, Cr, Mo, W, Cu, Ag, Zn, Cd, Fe, Ru, Co, Ir, Os, Ni, and oxides thereof, and other metal compounds or alloys thereof.

Different clad materials have different specificities to various chemical species. The specificity of different clads can be used to make simultaneous or multiple measurements which yield a better result by subtracting out the effects of other substances. Single waveguides can be clad with a plurality of different species-specific clad segments. Alternatively, multiple waveguide sensors each with a different species-specific clad could be in combination. The clad segments are chosen with various specificities so that information about the particular analyste of interest can be calculated from the detected signals from each sensor or from the plurality of clad segments on a single waveguide sensor.

DETAILED DESCRIPTION OF THE PREFERRED EMBODIMENTS

The invention is a waveguide sensor with at least one clad segment wherein the index of refraction of the waveguide segment and waveguide body have been selected relative to the index of the species of interest to produce a controlled leakage of light from the waveguide through the clad segment when the species of interest contacts the clad segment. The transmission properties of the waveguide thus vary as the refractive index of the species of interest present in the surrounding medium (in liquid or vapor or water emulsion form), and thus provide a measure of the refractive index. The clad segments are also chosen for their specificity to particular species of interest so that the sensor response identifies the species. The invention applies generally to all waveguide sensors and particularly to planar waveguides.

In accordance with the invention, the waveguide body and clad segment materials are selected with indices $N_1$, $N_3$ to optimize the effect of the refractive index of the chemical species of interest. Both selective affinity and refractive index must be considered to get required specificity and sensitivity. In a mixture it is the average refractive index which is measured, i.e., the refractive index is one number which is determined by all the species present and their concentrations. Sorting, or enhancing the response of a particular species or group of compounds, is thus a prerequisite to a refractive index measurement.

The proper matching of the refractive indexes $N_1$, $N_2$, $N_3$, $N_4$ in configuring the waveguide sensor forms a further part of the invention and produces an optimized sensor tailored to a particular species. The species of interest has a refractive index $N_4$. The clad segment is formed of a material with index $N_3$ which has a known affinity for the particular chemical species. When the species of interest contacts the clad segment on the waveguide, a refractive index $N^*$ is produced which is a function of both $N_3$ and $N_4$. The choice of the clad segment material, as well as various characteristics of the clad segment such as thickness and porosity, in combination with the chemical species of interest thus produce the refractive index $N^*$ seen by the waveguide sensor in the interaction region. For the waveguide to leak light, the index $N^*$ must be greater than $N_1$ so a suitable material for the waveguide can be selected. Once the waveguide material is selected, the remaining clad material with index $N_2$ can be selected. The index $N_2$ must be less than $N_1$ and is preferably at least about 10% less so that the critical angle is relatively large and a significant amount of the input light signal will be totally internally reflected down the waveguide. The index $N_2$ and the position of the clad segment(s) should also be selected so that a significant portion of the totally internally reflected light beam is incident on the clad segment(s).

Figure 1:
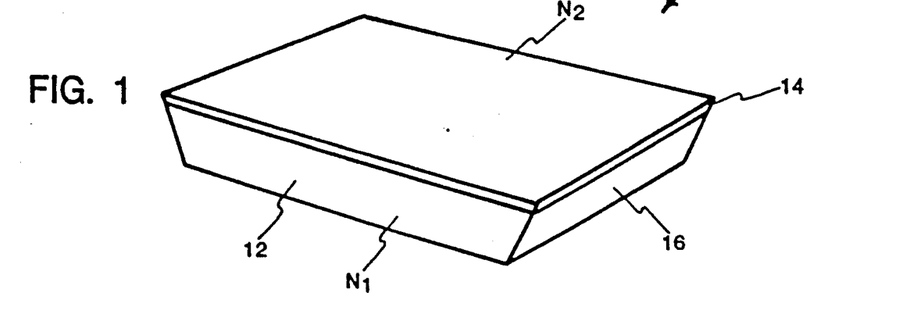
FIG. 1 is a perspective view of a planar waveguide having a clad formed thereon.

As shown in FIG. 1 an optical waveguide 10 is formed of a planar optical waveguide body 12 having a refractive index $N_1$ and a clad 14 having a refractive index $N_2$ less than $N_1$ formed thereon. The waveguide body 12 forms the light guiding means through which the light is guided, similar to the core of an optical fiber. The optical waveguide operates internal reflection of light at the waveguide body 12/clad 14 interface since the index $N_2$ is less than $N_1$ for all light within an angle determined by the ratio $N_2/N_1$. (Only details of the sensing surface containing clad 14 are shown, although the opposed surface would be mounted on a suitable substrate or be coated with a suitable coating to produce total internal reflection within the waveguide 12.) The waveguide 12 also has a pair of end surfaces 16 for inputting and outputting a light signal.

Figure 2:
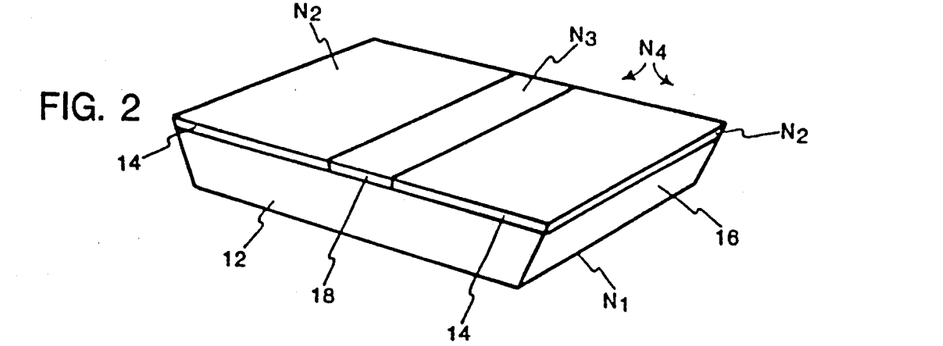
FIG. 2 is a perspective view of a planar waveguide having a clad formed thereon including a clad segment which introduce controlled light leakage.

As shown in FIG. 2, the clad 14 on waveguide body 12 contains a clad segment 18 of different refractive index $N_3$. With reference of FIG. 2, the chemical species of interest has an index $N_4$. The material of clad segment 18 is chosen so that it is specific to a species of interest and has an index $N_3$ which in combination with the index $N_4$ of the species of interest when present in the surrounding medium and the index $N_1$ of the waveguide produces a controlled light leakage from which the presence of the species of interest can be determined.

Although the entire clad 14 could in some circumstances be used for detecting the presence of the chemical species of interest, in most cases the clad 14 will contain at least one clad segment 18 which is specifically designed to perform that function while the clad 14 serves to guide the light wave within the waveguide. Only the segment(s) 18 interact with the species of interest and change the light transmission characteristics of the waveguide.

Figure 3A:
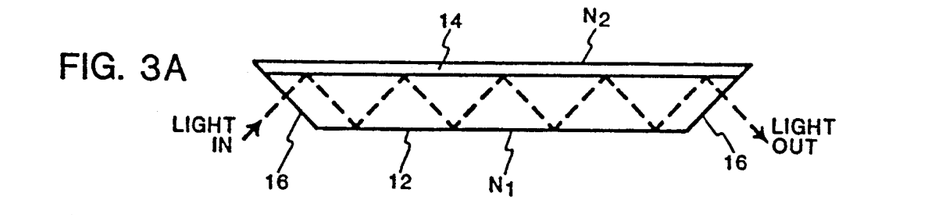
FIG. 3A and 3B are side views illustrating light transmission in the waveguides of FIGS. 1 and 2, respectively.
Figure 3B:
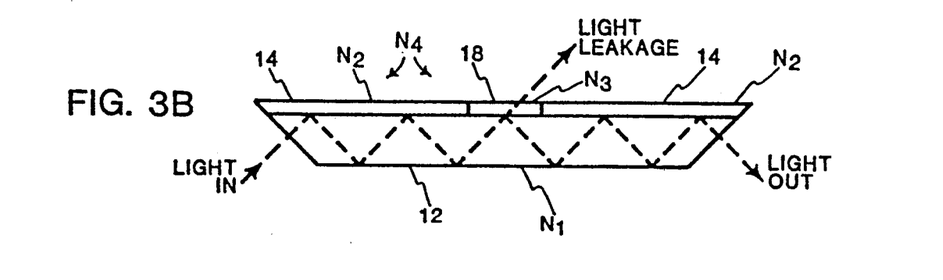

The operation of the waveguides of FIGS. 1 and 2 to transmit light are illustrated in FIGS. 3A and B, respectively. In FIG. 3A the light is input through one end face 16 of waveguide 12 and is totally internally reflected at the interface between waveguide 12 and clad 14 until it is output through the other end face 16. (As previously described, total internal reflection also occurs on the opposed surface of waveguide 12 from clad 14 by suitable means.) End faces 16 are preferably at angles as shown to eliminate light reflection on entrance and exit from the waveguide. In FIG. 3B, clad 14 continues to produce total internal reflection of the light within the waveguide 12 but clad segment 18 allows a controlled amount of the light to leak from the waveguide, thereby reducing the light output signal from the waveguide. Light leakage is controlled by the selection of the index N1 of the waveguide and index N3 of the clad segment so that in combination with the index N4 of the species of interest, the effect is optimized.

Figure 3C:
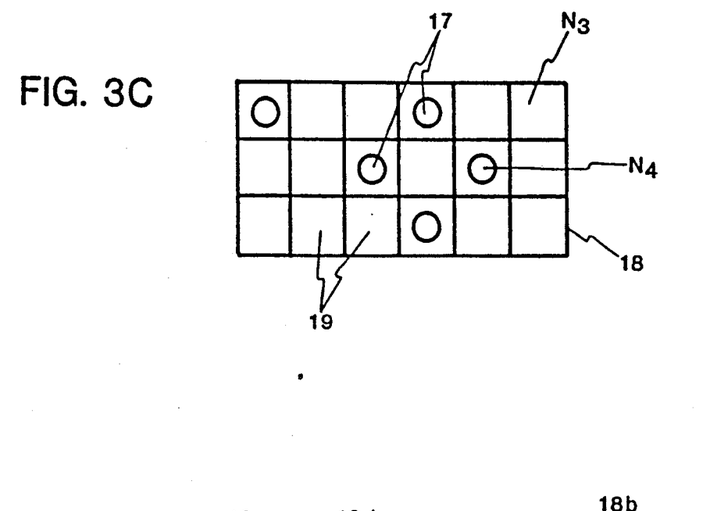
FIG. 3C is a top plane view of the clad segment of the waveguide of FIG. 2 showing clad porosity and absorption of sample molecules on the clad.

As illustrated in FIG. 3C, the light transmissivity or leakage is controlled by the clad segment 18 which is shown as having pores (cells) 19 into which atoms or molecules 17 of the species of interest are adsorbed. The combination of the clad 18 and adsorbed species 17 produces a localized refractive index which is used to control light leakage.

Figure 4:
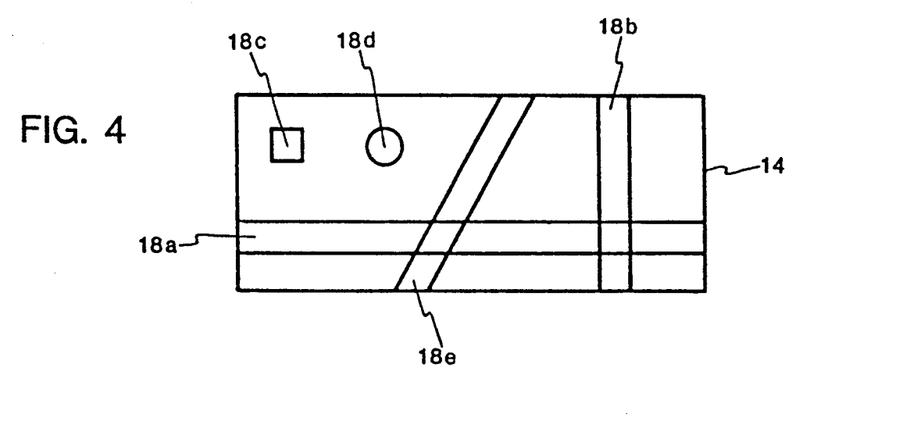
FIG. 4 is a top plan view of a planar waveguide showing various configurations and orientations of clad segments.

As illustrated in FIG. 4, the clad segments $18a,b,c,d,e$ can take a variety of shapes and orientations including stripes in any direction on the surface or square or circular areas. The ease of producing patterned coatings or a planar waveguide surface, using conventional technology such as photoresist, masking and etching from the semiconductor field, provides great flexibility in making clad segments which maximize contact with the sample.

Figure 5:
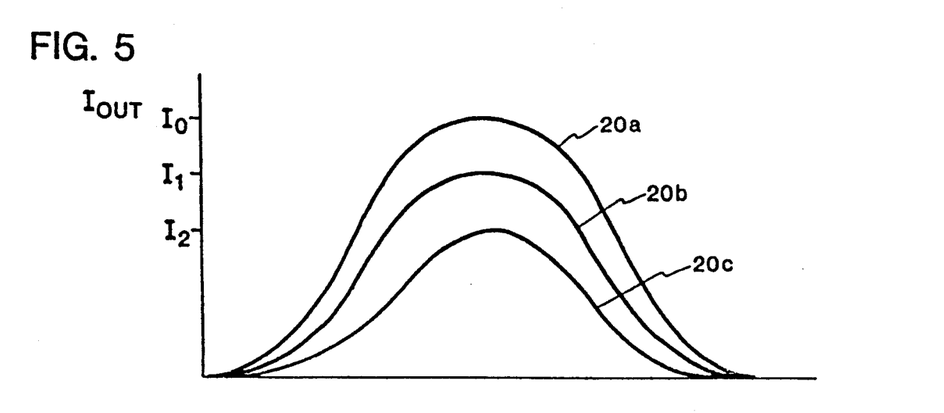
FIG. 5 is a graph of light output intensity as a function of light leakage.

The light intensity of the signal transmitted through the waveguide, thus will vary as a function of the presence of the chemical species of interest which causes a light loss during the transmission. The result of changes in the output signal are illustrated in FIG. 5. The dynamic range of the sensor is designed to provide easy measurement of the species in the concentration range of interest, i.e., the sensor is designed to produce a large signal change for a selected range of species concentration. By appropriate choice of the sensor parameters, the light loss that occurs over a measurement range of interest is a significant percentage of the total light signal (no loss) so that the signal difference can be easily measured. Choice of light intensity and wavelength also can be used to obtain the desired dynamic range.

Figure 6A:
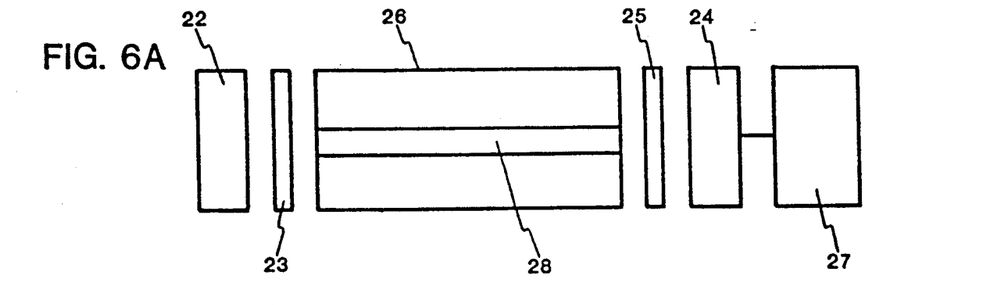
FIG. 6A is a schematic view of a measurement system using a planar waveguide with species-specific clad segment.

A simple sensor system 29 utilizing the waveguide sensor is illustrated in FIG. 6A. The waveguide 26 having a clad segment 28 formed thereon is placed between a source 22 and detector 24. Suitable optics 23, 25 such as lenses, filters, polarizers, etc. may be utilized between the source and detector and the waveguide, if necessary. The signal from detector 24 is input into processing means 27 such as a digital computer to record, display and otherwise process the signals. Although clad segment 28 is shown as a stripe oriented along the axis between the source and detector, other orientations or shapes of the clad segment could be used. When the surrounding medium which contacts the clad segment 28 on the surface of waveguide 26 contains a species of interest for which the waveguide 26/clad segment 28 have been designed, light leakage occurs so that the detected light intensity of the signal propagated through the waveguide decreases. Light sources including lasers (e.g. diode lasers), lamps or LEDs can be used. The detector may be a photodiode or laser diode.

Figure 6B:
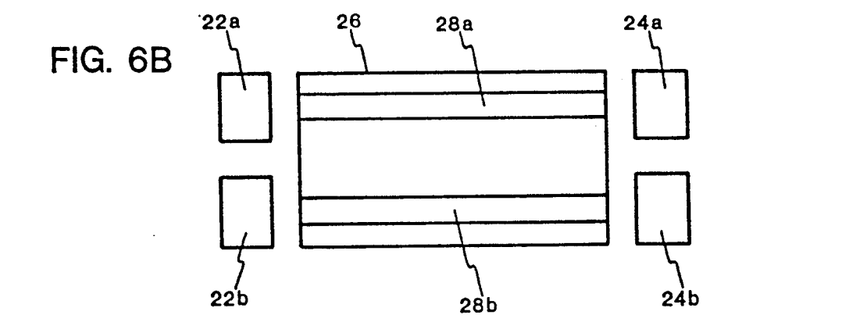
FIGS. 6B–F are various embodiment of measurement systems utilizing planar waveguides with two or more species-specific clad segments.

Various embodiments of the dual/multiple measurement approach are shown in FIGS. 6B-F. As shown in FIG. 6B, waveguide 26 is formed with a pair of spaced parallel clad segments $28a,b$ each of which has a different specificity to a particular chemical species or group of chemical species. A pair of sources $22a,b$ and a pair of detectors $24a,b$ are positioned around the waveguide 26, with one of each pair aligned with one of the clad segments $28a,b$. By using highly directional sources $22a,b$, or by using additional optics, the light beam from source $22a$ to detector $24a$ will be affected by clad segment $28b$ but not significantly by clad segment $28b$, and light from source $22b$ to detector $24b$ will be affected only by clad segment $28b$; i.e., the light beams from the two sources will propagate along separate channels or portions of the waveguide and each will only be affected by one clad segment. The output of detectors $24a,b$ can then be processed to provide desired information.

Alternative configurations include the use of a single source with a pair of detectors or a single detector with a pair of sources. The particular configuration will depend partly on the spectral characteristics of available sources and detectors. Using such arrangements, the effects of each of the clad segments $28a,b$ can be measured and the signals processed, e.g. by processing means 27 (FIG. 6A) such as a digital computer, to provide desired information about particular chemical species. Of course, the principles can be generalized to more than two clad segments.

Figure 6C:
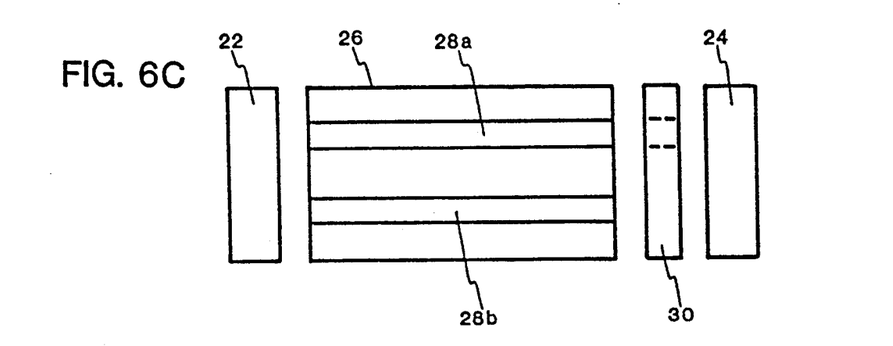

As shown in FIG. 6C, a waveguide 26 with spaced parallel clad segments $28a,b$ is positioned between a single source 22 and detector 24. A mechanical shutter or chopper 30 is positioned between the waveguide 26 and detector 24 in order to alternately pass the signal produced by one clad segment while blocking the effect produced by the other clad segment. In the configurations of 6B and C, the clad segments should be oriented parallel to the axis between the source and detector to define somewhat separate channels wherein different effects on signal transmission can be detected, either simultaneously (FIG. 6B) or alternately (FIG. 6C).

Figure 6D:
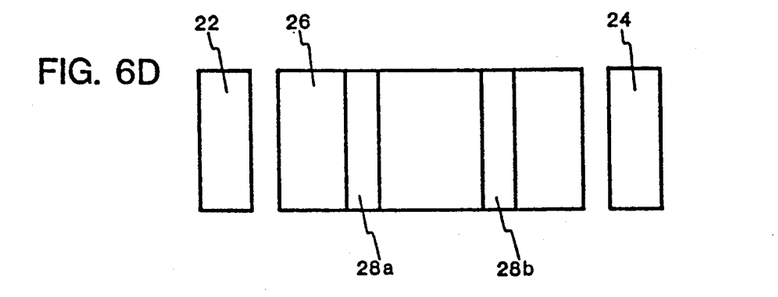

However, if suitable sources and detectors are available, a more general configuration of waveguide 26 with clad segments $28a,b$ can be positioned between a single source 22 and single detector 24 as shown in FIG. 6D. For example, dichromatic LED lamps and color sensors are available. The specificity and sensitivity of a clad segment to a chemical species can also be a function of the wavelength of the light. Thus, a light signal of two wavelengths, each of which is affected differently by the two clad segments can be input and the variation at the two frequencies can be detected. Alternatively, two sources of different wavelengths and/or two detectors can be used.

Figure 6E:
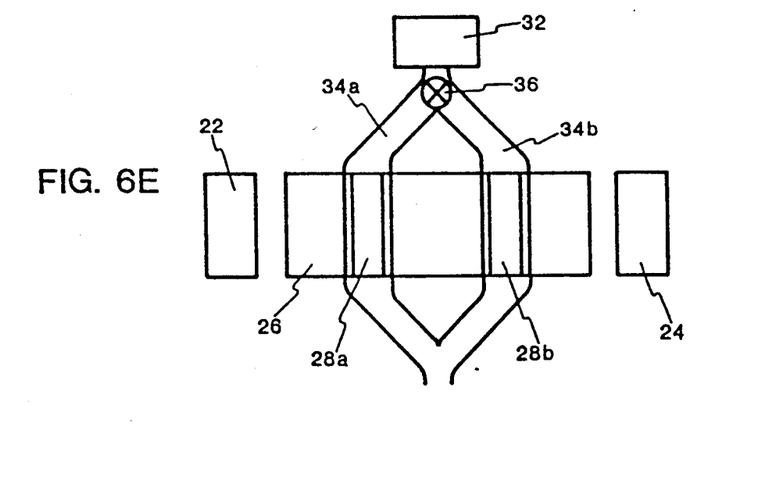
Figure 6F:
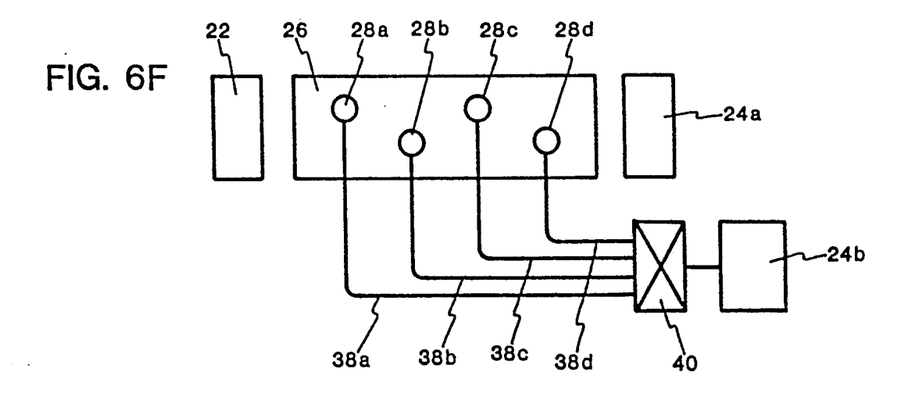

When the available sources and/or detectors do not allow simultaneous measurement of the effects produced by two different clad segment, it may be possible to perform sequential measurement of these effects. For example, as shown in FIG. 6E, the waveguide 26 with clad segments $28a,b$ is positioned between a source 22 and detector 24. Sample from reservoir 32 is flowed through a control valve 36 into a pair of flow channels 34a,b which contact clad segments 28a,b respectively. The sample can first be flowed through channel 34a to produce a response due to clad segment 28a and then flowed through channel 34b to produce a response due to clad segment 28b.

In addition to measuring the light transmitted through the waveguide, it is also possible to measure the light lost through the clad segment. For example, in FIG. 6F a waveguide has a plurality of circular clad segments 28a,b,c,d and is positioned between a source 22 and detector 24a. Fiber optic or other suitable detectors 38a,b,c,d are positioned to measure the light leakage through clad segments 28a,b,c,d, respectively. The signals from light sensors 38a,b,c,d pass through a multiplexor 40 into a second detector 24b so that the light leakage signals can be measured.

Figure 7:
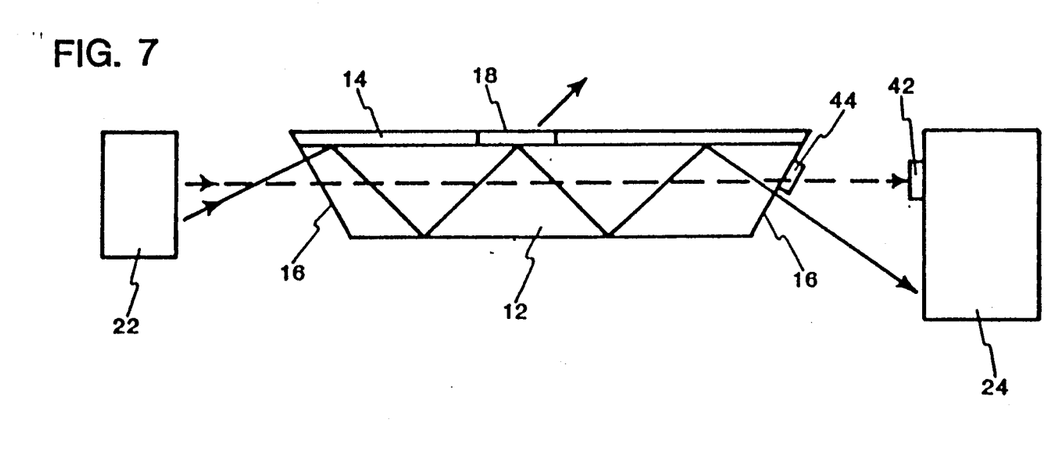
FIG. 7 is a side view of a planar waveguide measurement system including means for blocking light which propagates straight down the waveguide.

The ability to accurately measure the intensity changes caused by leakage through the clad segment is important. As shown in FIG. 7, a waveguide structure 12/14 with clad segment 18 is positioned between a source 22 and detector 24. Light from the source 22 which enters waveguide body 12 through end face 16 and is incident on clad 14 at an angle less than the critical angle defined by the refractive index ratio will be totally internally reflected as illustrated. However, some light will propagate substantially down the center of the waveguide; this is particularly so when source 22 is not highly directional. This unreflected light passes straight down the waveguide and provides a large background signal at detector 24. To reduce or eliminate this problem, detector masking means 42 can be positioned on detector 24 and/or detector masking means 44 can be positioned on end face 16 to substantially block the unreflected background light which passes straight down the center of the waveguide while permitting substantially all the totally internally reflected light to reach the detector.

Figure 8:
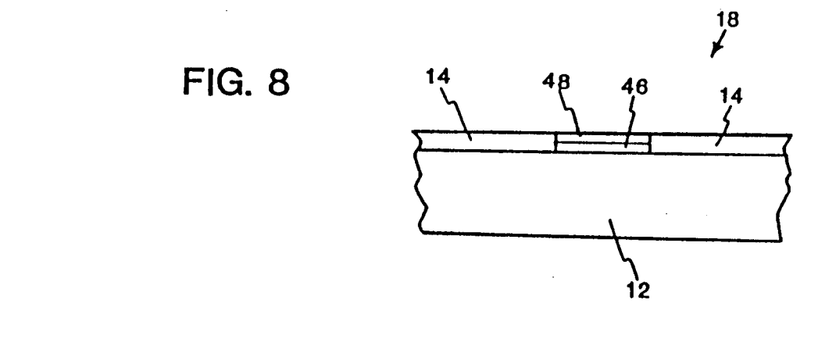
FIG. 8 is a side view of a waveguide with a clad segment formed of two layers of different materials.

The refractive index and sensitivity of the clad segment are important parameters of the waveguide sensor. However, in some circumstances the available materials may not provide the desired values. One approach, as illustrated in FIG. 8 is to form clad segment 18 of two different materials, e.g. a thin metal layer 46 overcoated by a polymer layer 48, or vice-versa, which together produce the desired properties. For example, metal layer 46 can be chosen for its affinity to the species and polymer 48 (which is permeable to the species) can provide the desired refractive index N3 of clad segment 18 (N3 will be determined by index N5 of layer 46 and index N6 of layer 48). The refractive index of select metals, at various wavelengths, are listed in Table 1 and the refractive index to select polymers is shown in Table 6. Combinations of these can be used as described.

A further possibility to provide selectivity of the clad segment where a suitable material is not available, but a good material is available which is specific to a reaction product of the species, is to include a catalyst in the clad segment. Clad segment 18 can include a catalyst embedded or dispersed therein, or a separate catalyst layer can be applied on the species-specific clad layer, e.g. in FIG. 8, layer 46 is the specific clad material and layer 48 is the catalyst. The catalyst will catalyze a reaction of the species of interest to form a reaction product to which the clad segment has strong affinity. As an example, TCE could be detected by a waveguide sensor having a clad segment specific to HCl and a catalyst to react with the TCE to form HCl.

In accordance with the invention, the principles of application Ser. No. 07/501,144 relating to the use of thin film metal clads and dual measurement techniques using species-specific metal clads of different specificity has been generalized from fiber optic waveguides to all waveguides, particularly planar waveguides. The specific or affinity of the clad has been further defined in terms of various parameters, particularly surface structure as well as crystallographic orientation. A methodology for tailoring a waveguide sensor to a particular chemical species by appropriate choice of the refractive indices is provided. Multiple clad segments are used to identify a particular species from a group species which interact with some clad materials. A clad segment of two different materials, one to provide refractive index and the other to provide species selectivity, can be used, as well as a clad segment with a catalyst to react the species of interest to provide a reaction product for which the clad segment has a strong affinity.

The substrate is usually glass or quartz. This material has a refractive index of 1.47(6) at 400 nm, 1.46 (2) at 500 nm and 1.45(7) at 650 nm. Special substrates can be made of a variety of materials, e.g., NaCl, N=1.54(4); AgCl, N=2.07(1); $Ag_2SO_4$, N=1.75(8); $MgF_2$, N=1.378; $Li_2SO_4$, N=1.46(5), and $Al_2(SO_4)_3$, N=1.47. In fact, any material which can be made into a plate which can propagate light is a possible substrate.

In the waveguide structures according to the invention, the clad segments are typically about a monolayer to about 50 Å thick. The waveguide body must have sufficient rigidity so that the light propagation pattern is not affected by flexing.

A preferred type of clad that may be utilized for the clad segments on the refractive index based waveguide sensor is the metal clad disclosed in U.S. patent application Ser. No. 07/501,144, now U.S. Pat. No. 5,026,139 which is herein incorporated by reference. These thin metal clads can be chosen with an effective light porosity or transmissivity when in contact with a species of interest of change the light transmission through the waveguide as a function of the refractive index of the chemical species of interest present in the surrounding medium. The light porosity of the clad is a function of the clad material, its thickness and its physical characteristics such as physical porosity and crystalline structure. The metal clad is selected of a suitable thickness to produce a gradient refractive index at the interface between the waveguide body and the clad segment as a result of chemical species of interest from the surrounding medium being adsorbed on the metal clad. This localized refractive index at the boundary between the waveguide body and clad segment is directly proportional to the amount of the chemical species adsorbed/absorbed on the clad segment and also its refractive index. The amount of light leaking from the waveguide through the clad depends on the amount and refractive index of the chemical species. The light leakage substantially modulates the light signal transmitted through the core, producing a detectable measure of the presence of the chemical species and its refractive index.

The metal coatings are key to the selection process. They are selected both because they have specific affinity to various species and because they have appropriate refractive indices. The index of refraction of several metals, for several wavelengths, are given in Table 1.

TABLE 1

| Wavelength (nm) | Photon Energy (ev) | Refractive Index | | | |
| --- | --- | --- | --- | --- | --- |
| | | (Cr) | (Ni) | (Rh) | (Pt) |
| 990 | 1.25 | 4.50 | 2.91 | 3.39 | 3.42 |
| 660 | 1.88 | 3.66 | 2.10 | 2.22 | 2.48 |
| 550 | 2.26 | 3.31 | 1.78 | 1.98 | 2.13 |
| 480 | 2.59 | 2.22 | 1.65 | 1.85 | 1.92 |

The affinity depends on the metal selected, the thickness of the coating and the method of attachment. The crystal structure and orientation is very important in the selectivity process. Furthermore, the more ordered the crystal, the better it behaves as a sensing material, e.g., Ni(111) and Ir(110) both adsorb benzene, but the Ni(111) is ordered while the Ir(110) is disordered and the Ni(111) performs much better. The type of adsorption, i.e., mechanical, chemical, electrostatic, solvation, etc. also determines the effectiveness of the metal coating.

The metal claddings that may be utilized as the clad segments on the waveguide include:
1) group IVB elements: Titanium (Ti), Zirconium (Zr), Hafnium (Hf)
2) group IVB elements: Vanadium (V), Niobium (Nb), Tantalum (Ta)
3) group IVB elements: Chromium (Cr), Molybdenum (Mo), Tungsten (W)
4) group IB elements: Copper (Cu), Silver (Ag), Gold (Au)
5) group IIB elements: Zinc (Zn), Cadmium (Cd)
6) group VIII elements: Iron (Fe), Ruthenium (Ru), Cobalt (Co), Rhodium (Rh), Nickel (Ni), Palladium (Pd), Platinum (Pt), Iridium (Ir), Osmium (Os)
7) Oxides of the above metals
8) Metal compounds or alloys such as:
   a) group II-VI compounds: including but not limited to ZnSe, ZnTe, CdS, CdTe, MgTe, ZnS
   b) group III-V compounds: including but not limited to BN, GaAs, InAs, InSb, AlN, GaN, InN
   c) group I-VII compounds: including but not limited to CuCl, CuBr, AgI
   d) sphalerite structure compounds: including but not limited to $Ga_2Te_3$, $ZnSnP_2$, $ZnSnAs_2$
   e) Wurtzite structure compounds: including but not limited to Sic, MnS, MnSe, MnTe, $Al_2Se_3$
   f) group I, III, VI compounds: including but not limited to $CuGaTe_2$, $CuGaSe_2$, $CuLaS_2$
   g) group II, IV, V compounds: including but not limited to $ZnGeP_2$, $CdGeP_2$, $ZnGeAs_2$, $ZnSnAs_2$ The metal coatings can be deposited on the waveguide surface by sputtering, brush coating, vacuum deposition, plasma coating or by any other technique that can form either a homogeneously or heterogeneously coated surface. Various lithographic techniques can be used to produce the appropriate clad segment patterns. Either inorganic or organometallic compounds can be used to deposit metal coatings on the waveguide. The metals can also be deposited from their elemental states. The final coating deposited on the waveguide can be in the form of either elemental metal or any of its oxides or other metal compounds or alloys.

The clad segments are made of material which have a strong affinity for the chemical species of interest. The affinity is determined by a number of different factors such as chemical or mechanical adsorption, pore size, electrostatic attraction, or ability to dissolve the species. The affinity of the clad segment for the species is illustrated in FIG. 3C in which atoms or molecular 17 of the species are adsorbed in pores 19 (indicated by cell structure) formed in clad segment 18.

The metal clads show varying sensitivities or selectivities for different chemical species. The variation of sensor response to various chemical species is illustrated in Table 2 where $V_0$ is the detector voltage output in the absence of the chemical species (i.e., no light leakage) and V is the detector output voltage in the presence of a given amount of the chemical species. Certain metals are particularly sensitive to certain chemical species while relatively insensitive to others. Each chemical species can be detected by a number of different metal clads.

TABLE 2

| | $V_0$ | V |
| --- | --- | --- |
| Ru | | |
| Gasoline | 7.27 | 3.87 |
| Benzene | 7.00 | 4.19 |
| Xylene | 7.38 | 4.39 |
| Toluene | 7.07 | 4.10 |
| V | | |
| Gasoline | 6.85 | 5.80 |
| Benzene | 5.32 | 3.79 |
| Zr | | |
| Gasoline | 8.20 | 5.89 |
| Benzene | 8.00 | 2.28 |
| Xylene | 7.68 | 3.62 |
| Toluene | 7.51 | 4.57 |
| Ni | | |
| Gasoline | 9.46 | 6.74 |
| Benzene | 7.48 | 1.07 |
| Xylene | 8.56 | 1.27 |
| Toluene | 8.16 | 1.77 |
| Pd | | |
| Gasoline | 7.51 | 4.92 |
| Benzene | 8.00 | 6.78 |
| Xylene | 7.44 | 5.00 |
| Fe | | |
| Benzene | 8.96 | 1.65 |

Table 3 lists a number of illustrative metal surfaces and various gases which have been found to be adsorbed on the metal surface. The adsorbability of the gases may depend on the crystal form and/or orientation of the metal layer. In the process of forming the metal clad segment on the waveguide, particular crystal forms of the metal can be reproducibly obtained by controlling the process parameters, e.g. temperature and pressure, so that a sensor tailored to a specific gas can be obtained. Thus, a sensor with a metal clad segment of preselected crystal structure can be produced for use with a desired analyte. Table 4 similarly lists a number of illustrative metal surfaces and various organic compounds (hydrocarbons) which have been found to be adsorbed on the metal surface. Certain metals, and in some cases certain crystal forms of some metals, are thus particularly suitable for the metal clad segment for detection of certain hydrocarbons. The lists in Tables 3 and 4 are only for purposes of illustration and are not exhaustive of all possible combinations. Further information about adsorption of gases by metal surfaces is contained in *Chemistry In Two-Dimensional Surfaces*, Gabor A. Somorjai, Cornell Univ. Press, Ithaca, N.Y., 1981 particularly Tables 5.2–5.7, pp. 210–241 which are herein incorporated by reference.

TABLE 3

| SURFACE | | ADSORBED GAS |
|---|---|---|
| Al | (111), (100), 110) | $O_2$ |
| Au | (111) | $O_2$ |
| | (100) | $H_2S$, CO, Xe |
| Cu | (111) | $O_2$, CO, $Cl_2$, $H_2S$, Xe |
| | (100) | $O_2$, CO, $N_2$ |
| | (110) | $O_2$, CO, $H_2O$, $H_2S$, Xe |
| Cu/Ni | (111) | CO |
| | (110) | $O_2$, CO, $H_2S$ |
| Fe | (111) | $O_2$, $NH_3$, $H_2$ |
| | (100) | $O_2$, CO, $H_2S$, $H_2$, $NH_3$, $H_2O$ |
| | (110) | $O_2$, CO, $N_2$, $H_2$, $H_2S$ |
| Fe/Cr | (100), (110) | $O_2$ |
| Mo | (111) | $O_2$, $H_2S$ |
| | (100) | $O_2$, CO, $H_2$, $N_2$, $H_2S$ |
| | (110) | $O_2$, CO, $CO_2$, $H_2$, $N_2$, $H_2S$ |
| Ni | (111) | $O_2$, CO, $CO_2$, $H_2$, NO, $H_2S$, $H_2Se$, $Cl_2$ |
| | (100) | $O_2$, CO, $CO_2$, $H_2$, $H_2S$, Te, Xe |
| | (110) | $O_2$, CO, $H_2$, NO, $H_2O$, $H_2S$, $H_2Se$ |
| NiO | (101) | $H_2$, $H_2S$, $Cl_2$ |
| Pt | (111) | $O_2$, CO, $H_2$, NO, $H_2O$, $S_2$, N |
| | (100) | $O_2$, CO, $H_2$, NO, N, $H_2S$, $S_2$ |
| | (110) | $O_2$, CO, $C_3O_2$, NO, $H_2S$ |
| Rh | (111), (100) | $O_2$, CO, $CO_2$, $H_2$, NO |
| | (110) | $O_2$, CO |
| Zn | (0001) | $O_2$ |
| ZnO | (1010) | $O_2$ |

TABLE 4

| SURFACE | | ADSORBED GAS |
|---|---|---|
| Fe | (100) | $C_2H_4$ |
| Ir | (111) | $C_2H_2$, $C_2H_4$, cyclohexane, benzene |
| | (100) | $C_2H_2$, $C_2H_4$, benzene |
| | (110) | $C_2H_4$, benzene |
| Mo | (100) | $CH_4$ |
| Ni | (111) | $CH_4$, $C_2H_2$, $C_2H_4$, $C_2H_6$, cyclohexane, benzene |
| | (100) | $CH_4$, $C_2H_2$, $C_2H_4$, $C_2H_6$, benzene |
| | (110) | $CH_4$, $C_2H_4$, $C_2H_6$, $C_5H_{12}$ |
| Pt | (111) | $C_2H_2$, $C_2H_4$, n-butane, n-pentane, n-hexane, n-heptane, n-octane, cyclohexane, benzene, toluene, naphthalene, pyridine, m-xylene, mesitylene, T-butylbenzene, N-butylbenzene, aniline, nitrobenzene, cyanobenzene |
| | (100) | $C_2H_2$, $C_2H_4$, benzene, naphthalene, pyridine, toluene, M-xylene, mesitylene, T-butylbenzene, N-butylbenzene, aniline, nitrobenzene, cyanobenzene, $C_2N_2$ |
| | (110) | HCN, $C_2N_2$ |
| Rh | (111), (100), (331) | $C_2H_2$, $C_2H_4$ | the specificity of different metal clads to various analytes allows more specific analysis of an analyte mixed with other substances. The invention further includes multiple measurement methods and apparatus. Since more than one clad may be available for a particular analyte, but each clad will not have the same absorption coefficients to other analytes, a more complex measurement method and sensor structure can be used to determine the presence of a selected analyte out of a mixture of several different analytes. To detect analyte A in a mixture of analytes A and B, it would be most desirable to find a single metal surface that is specific to A. However, if one cannot be found, two sensors can be used, one which has a clad which responds to both A and B and one which has a clad which responds to B but not A. By subtracting the measurement obtained from the second sensor from that of the first sensor, a measure of analyte A is obtained.

Alternatively, if a specific metal clad is not available for either A or B, then clads are chosen which have different absorption coefficients for A and B, and the concentration of A and B are obtained by solving an algorithm for two unkowns. The dual sensor approach can be extended to multiple sensors for more than two analytes and can be implemented in a variety of ways, using either a single waveguide or multiple waveguides.

The crystallographic orientation of the metal coatings is particularly important since the affinity of various chemical species is often strongly dependent on the crystallographic form of the metal. The planar waveguide is a highly advantageous structure for depositing clad segments having preferred crystallographic orientations, since deposition on a flat surface is much easier to perform using known deposition techniques.

As shown in Table 5, pairs of clad segments, each responsive to different combinations of different chemical species, can be used to detect a particular species by subtracting one response from another when a particular clad which responds directly to a single species is not available.

TABLE 5

| | |
|---|---|
| Be (0001) | $O_2$, CO, $H_2$, $N_2$ |
| Cu (100) | $O_2$, CO, $N_2$ |
| [Be (0001)] − [Cu (100)] | $H_2$ |
| Mo (100) | $O_2$, CO, $H_2$, $N_2$, $H_2S$ |
| Be (0001) | $O_2$, CO, $H_2$, $N_2$ |
| [Mo (100)] − [Be (0001)] | $H_2S$ |
| Co (100) | CO, $O_2$ |
| Cr (100) | $O_2$ |
| [Co (100)] − [Cr (100)] | CO |
| Mo (110) | $O_2$, CO, $CO_2$, $H_2$, $N_2$, $H_2S$ |
| Mo (100) | $O_2$, CO, $H_2$, $N_2$, $H_2S$ |
| [Mo (110)] − [Mo (100)] | $CO_2$ |
| Ru (101) | $O_2$, CO, NO |
| Co (100) | $O_2$, CO |
| [Ru (101)] − [Co (100)] | NO |

In addition to the crystallographic orientation of the surface, the surface structure itself provides specificity. For example P(111) adsorbs n-butane, n-pentane, n-hexane and n-octane. If the surface structures are considered, preference can be attained. The preferred structures of the Pt(111) surface for these species are:

$$\text{n-butane} \begin{pmatrix} 2 & 1 \\ -1 & 2 \end{pmatrix}$$

$$\text{n-pentane} \begin{pmatrix} 2 & 1 \\ 0 & 6 \end{pmatrix}$$

$$\text{n-hexane} \begin{pmatrix} 2 & 1 \\ 0 & 8 \end{pmatrix}$$

$$\text{n-octane} \begin{pmatrix} 2 & 1 \\ -1 & 4 \end{pmatrix}$$

For these linear molecules, therefore, $$\begin{pmatrix} 2 & 1 \\ x & y \end{pmatrix}$$

is the general surface structure. It is important to note that for cyclohexane, this changes and the surface structure becomes Table 7, proper selection of overcoating makes species concentrations available by difference.

TABLE 7

| Species | Compound | $N_c$ | Typical Overcoat | $N_o$ | Measured Species |
|---|---|---|---|---|---|
| 1 | Chloroform | 1.448 | Cellulose acetate butyrate | 1.460 | 1 |
| 2 | TCE | 1.477 | Poly(n-butyl methacrylate) | 1.480 | 1 + 2 |
| 3 | 4-chlorophenol | 1.541 | Poly(N-allyl methacrylate) | 1.547 | 1 + 2 + 3 |
| 4 | 3-chlorophenol | 1.556 | Epoxy Resin | 1.557 | 1 + 2 + 3 + 4 |
| 5 | 2-chlorophenol | 1.557 | Poly(benzyl methacrylate) | 1.568 | 1 + 2 + 3 + 4 + 5 |

$$\begin{pmatrix} 4 & -1 \\ 1 & 5 \end{pmatrix}.$$

Therefore, according to the invention, by forming a clad segment of a particular material, with a particular crystallographic orientation and a specific surface structure, specificity for individual species can be better achieved.

The Pt(111) example illustrates the use of different surface structures of a material to select between closely related compounds with similar structures. The ability to distinguish between compounds with very similar chemical structures, without doing a detailed spectral analysis, is very important to sensor technology. The same approach is applicable to separate benzene, toluene and xylene.

Whereas the surface structures give good species separation, improvements can be made on specificity by further focusing on refractive index differences. This can be accomplished in two (2) ways: (i) undercoating or overcoating the metal film and (ii) adjusting the refractive index of the substrate (N1) by selecting a suitable material for the substrate.

The overcoating (or undercoating) of the metal film will, among other materials, be a polymer. These materials, nominally, have refractive indices between 1.34 and 1.64. Examples of these are given in Table 6.

TABLE 6

| Compound | Refractive Index |
|---|---|
| Poly(tetrafluoroethylene-co-hexafluoropropylene) | 1.338 |
| Poly(pentafluoropropyl acrylate) | 1.385 |
| Poly(butyl acrylate) | 1.466 |
| Poly(n-butyl methacrylate) | 1.481 |
| Cellulose Nitrate | 1.500 |
| Poly (N-benzyl methacrylamide) | 1.596 | p It is possible to find metal surfaces which will selectively adsorb target compounds. This can range from a single species to a group of compounds. These surfaces are anything but perfect when it comes to completely isolating a particular target and secondary species sorting may help. As an example, in environmental analysis, separation and analysis of the organic chlorides is an important task. Typical compounds are chloroform [N=1.448(6)], trichloroethylene (TCE) [N=1.477(5)], and the chlorophenols [$N_{2\text{-}chloro}$=1.557(9), $N_{3\text{-}chloro}$=1.556(5), $N_{4\text{-}chloro}$=1.541(9)]. The metal is chosen to selectively adsorb the organic chlorides while an overcoating (or undercoating) is used to control light leakage. For the above compounds, if the overcoating has 1.448<N<1.477 (e.g., cellulose acetate butyrate) only the chloroform controls the light. As shown in Table 7, proper selection of overcoating makes species concentrations available by difference.

For example, to obtain inputs on 3-chlorophenl (species 4) subtract 3 from 4, i.e., [(1+2+3+4)−(1+2+3)=4 ].

Changes and modifications in the specifically described embodiments can be carried out without departing from the scope of the invention which is intended to be limited only by the scope of the appended claims.

We claim:

1. A waveguide sensor for measuring refractive index and identifying chemical species of a surrounding medium, comprising:

a light guiding means having a refractive index N1 wherein the light guiding means is a planar waveguide body;

a clad having a thin film metal clad segment of metal or metal oxide or other metal compound or alloy formed on a portion of the light guiding means, the metal clad segment having a refractive index N3 and an effective thickness and light transmissivity which in combination with the surrounding medium produces a localized refractive index and a controlled leakage of light which modulates the transmission of light through the light guiding means as a function of the refractive index of the surrounding medium, the remainder of the clad having a refractive index N2 less than N1.

2. The sensor of claim 1 further comprising:

a light source operatively associated with the light guiding means for inputting a light signal into the light guiding means;

detection means operatively associated with the light guiding means for detecting a light signal from the light guiding means.

3. The sensor of claim 1 wherein the metal clad segment is selected from:

a) group IB elements: Copper (Cu), Silver (Ag), Gold (Au)

b) group IIB elements: Zinc (Zn), Cadmium (Cd)

c) group IVB elements: Titanium (Ti), Zirconium (Zr), Hafnium (Hf)

c) group VB elements: Vanadium (V), Niobium (Nb), Tantalum (Ta)

d) group VIB elements: Chromium (Cr), Molybdenum (Mo), Tungsten (W)

f) group VIII elements: Iron (Fe), Ruthenium (Ru), Cobalt (Co), Rhodium (Rh), Nickel (Ni), Palladium (Pd), Platinum (Pt), Iridium (Ir), Osmium (Os)

g) oxides of the above metals;

h) group II-VI compounds: ZnSe, ZnTe, CdS, CdTe, MgTe, ZnS;

i) group III-V compounds: BN, GaAs, InAs, InSb, AlN, GaN, InN;

j) group I-VII compounds: CuCl, CuBr, AgI;

k) sphalerite structure compounds: $Ga_2Te_3$, $ZnSnP_2$, $ZnSnAs_2$;

l) Wurtzite structure compounds: SiC, MnS, MnSe, MnTe, $Al_2Se_3$;

m) group I, III, VI compounds: $CuGaTe_2$, $CuGaSe_2$, $CuLaS_2$;

n) group II, IV, V compounds: $ZnGeP_2$, $CdGeP_2$, $ZnGeAs_2$, $ZnSnAs_2$.

4. The sensor of claim 1 wherein the metal clad segment has a preselected crystallographic orientation which is specific to a chemical species of interest.

5. The sensor of claim 1 wherein the metal clad segment has a preselected surface structure which is specific to a chemical species of interest.

6. The sensor of claim 5 wherein the metal clad segment is formed of Pt(111) with a surface structure selected from $$\begin{pmatrix} 2 & 1 \\ -1 & 2 \end{pmatrix}, \begin{pmatrix} 2 & 1 \\ 0 & 6 \end{pmatrix}, \begin{pmatrix} 2 & 1 \\ 0 & 8 \end{pmatrix}, \begin{pmatrix} 2 & 1 \\ -1 & 4 \end{pmatrix} \text{ and } \begin{pmatrix} 4 & -1 \\ 1 & 5 \end{pmatrix}.$$

7. The sensor of claim 1 further comprising a plurality of metal clad segments, each having different selectivity to chemical species of interest.

8. The sensor of claim 7 further comprising:
a light source operatively associated with the light guiding means for inputting a light signal into the light guiding means;
detection means operatively associated with the light guiding means to detect signals produced by modulation by each metal clad segment;
processing means for calculating information about a particular compound of interest from the signals produced by modulation by the metal clad segments.

9. The sensor of claim 7 comprising a pair of metal clad segments selected from:
 a) Be (0001) and Cu(100);
 b) Mo (100) and Be (0001);
 c) Co (100) and Cr (100);
 d) Mo (110) and Mo (100);
 e) Ru (101) and Co (100);
and further comprising means for detecting a signal produced by each of the pair of metal clad segments and means for subtracting the signals produced by each of the pair of metal clad segments.

10. The sensor of claim 1 wherein the waveguide body is formed of $SiO_2$ (glass/quartz), NaCl, AgCl, $Ag_2SO_4$, $MgF_2$, $Li_2SO_4$ and $Al_2(SO_4)_3$.

11. A waveguide sensor for measuring refractive index and identifying chemical species of a surrounding medium, comprising:
a light guiding means having a refractive index N1; a clad having a thin film metal clad segment of metal or metal oxide or other metal compound or alloy formed on a portion of the light guiding means, the metal clad segment having a refractive index N3 and an effective thickness and light transmissivity which in combination with the surrounding medium produces a localized refractive index and a controlled leakage of light which modulates the transmission of light through the light guiding means as a function of the refractive index of the surrounding medium, the remainder of the clad having a refractive index N2 less than N1;
an overlayer or underlayer of a second material on the metal clad segment, the metal clad segment having a strong affinity for a chemical species of interest, the second material having a suitable refractive index to produce controlled light leakage in the presence of the chemical species.

12. The sensor of claim 11 wherein the light guiding means is a planar waveguide body.

13. The sensor of claim 11 wherein the second material is a polymer with a refractive index in the range of about 1.34 to about 1.64.

14. The sensor of claim 13 wherein the polymer is selected from poly(tetrafluoroethylene-co-hexafluoropropylene), poly(pentafluoropropyl acrylate), poly(butyl acrylate), poly(n-butyl methacrylate), cellulose nitrate, and poly (N-benzyl methacrylamide).

15. The sensor of claim 11 wherein the metal clad segment adsorbs organic chlorides, and the second material is selected from cellulose acetate butyrate, poly(n-butyl methacrylate), poly(N-allyl methacrylate), epoxy resin, and poly(benzyl methacrylate).

16. A waveguide sensor for measuring refractive index and identifying chemical species of a surrounding medium, comprising:
a light guiding means having a refractive index N1; a clad having a thin film metal clad segment of metal or metal oxide or other metal compound or alloy formed on a portion of the light guiding means, the metal clad segment having a refractive index N3 and an effective thickness and light transmissivity which in combination with the surrounding medium produces a localized refractive index and a controlled leakage of light which modulates the transmission of light through the light guiding means as a function of the refractive index of the surrounding medium, the remainder of the clad having a refractive index N2 less than N1;
a catalyst on the metal clad segment for reacting with the species of interest to form a reaction product, wherein the metal clad segment is specific to the reaction product.

17. The sensor of claim 16 wherein the light guiding means is a planar waveguide body.

18. The sensor of claim 16 further comprising:
a light source operatively associated with the light guiding means for inputting a light signal into the light guiding means;
detection means operatively associated with the light guiding means for detecting a light signal from the light guiding means.

19. The sensor of claim 16 wherein the catalyst reacts with TCE to form HCl and the metal clad segment is specific to HCl.

20. A method of detecting the refractive index and identifying chemical species of a medium, comprising:
providing a waveguide sensor comprising light guiding means having a refractive index N1, and a clad having a thin film metal clad segment o metal or metal oxide or other metal compound or alloy formed on a portion of the light guiding means, the metal clad segment having a refractive index N3 and an effective thickness and light transmissivity which in combination with a surrounding medium produces a localized refractive index and a controlled leakage of light which modulates the transmission of light through the light guiding means as a function of the refractive index of the surrounding medium, the remainder of the clad having a refractive index N2 less than N1 wherein the light guiding means is formed of a planar waveguide body;

contacting the thin film metal clad segment with the medium; inputting a light signal into the light guiding means; detecting the changes in intensity of a light signal transmitted from the light guiding means.

21. The method of claim 20 wherein the metal clad segment from;
   a) group IVB elements; Titanium (Ti), Zirconium (Zr), Hafnium (Hf);
   b) group VB elements; Vanadium (V), Niobium (Nb), Tantalum (Ta);
   c) group VIB elements: Chromium (Cr), Molybdenum (Mo), Tungsten (W);
   d) group IB elements; Copper (Cu), Silver (Ag), Gold (Au);
   e) group IIB elements: Zinc (Zn), Cadmium (Cd);
   f) group VIII elements; Iron (Fe), Ruthenium (Ru), Cobalt (Co), Rhodium (Rh), Nickel (Ni), Palladium (Pd), Platinum (Pt), Iridium (Ir), Osmium (Os).

22. The method of claim 20 wherein the metal clad segment is a species-specific metal clad segment.

23. The method of claim 20 further comprising forming the metal clad segment with a preselected crystallographic orientation which is specific to a chemical species of interest.

24. The method of claim 20 further comprising forming the metal clad segment with a preselected surface structure which is specific to a chemical species of interest.

25. The method of claim 20 further comprising forming a plurality of metal clad segments, each having a different selectivity to chemical species of interest.

26. The method of claim 25 wherein the step of detecting comprises detecting changes in intensity produced by each of the plurality of segments and comparing the changes in intensity produced by each of the plurality of segments to determine the presence of a species of interest.

27. A method of detecting the refractive index and identifying chemical species of a medium, comprising:
   providing a waveguide sensor comprising light guiding means having a refractive index N1, and a clad having a thin film metal clad segment of metal or metal oxide or other metal compound or alloy formed on a portion of the light guiding means, the metal clad segment having a refractive index N3 and an effective thickness and light transmissivity which in combination with a surrounding medium produces a localized refractive index and a controlled leakage of light which modulates the transmission of light through the light guiding means as a function of the refractive index of the surrounding medium, the remainder of the clad having a refractive index N2 less than N1;
   forming an overlayer or underlayer of a second material on the metal clad segment, the metal clad segment having a strong affinity for a chemical species of interest, the second material having a suitable refractive index to produce controlled light leakage in the presence of the chemical species;
   contacting the thin film metal clad segment with the medium;
   inputting a light signal into the light guiding means;
   detecting the changes in intensity of a light signal transmitted from the light guiding means.

28. The method of claim 27 comprising forming the light guiding means of a planar waveguide body.

29. A method of detecting the refractive index and identifying chemical species of a medium, comprising:
   providing a waveguide sensor comprising light guiding means having a refractive index N1, and a clad having a thin film metal clad segment of metal or metal oxide or other metal compound or alloy formed on a portion of the light guiding means, the metal clad segment having a refractive index N3 and an effective thickness and light transmissivity which in combination with a surrounding medium produces a localized refractive index and a controlled leakage of light which modulates the transmission of light through the light guiding means as a function of the refractive index of the surrounding medium, the remainder of the clad having a refractive index N2 less than N1;
   adding a catalyst to the metal clad segment for reacting the species of interest to form a reaction product and forming the metal clad segment specific to the reaction product;
   contacting the thin film metal clad segment with the medium;
   inputting a light signal into the light guiding means;
   detecting the changes in intensity of a light signal transmitted from the light guiding means.

30. A method of forming a refractive index waveguide chemical sensor comprising:
   providing a planar waveguide body of refractive index N1;
   forming a clad on the waveguide body, the clad having a thin film metal clad segment of metal or metal oxide or other metal compound or alloy on a portion of the waveguide body, the metal clad segment having a refractive index N3 and an effective thickness and light transmissivity which in combination with a surrounding medium produces a localized refractive index and a controlled leakage of light which modulates the transmission of light through the waveguide body as a function of the refractive index of the surrounding medium, the remainder of the clad having a refractive index N2 less than N1.

31. The method of claim 30 comprising forming the metal clad of a metal selected from:
   a) group IB elements: Copper (Cu), Silver (Ag), Gold (Au);
   b) group IIB elements: Zinc (Zn), Cadmium (Cd);
   c) group IVB elements: Titanium (Ti), Zirconium (Zr), Hafnium (Hf);
   d) group VB elements: Vanadium (V), Niobium (Nb), Tantalum (Ta);
   e) group VIB elements: Chromium (Cr), Molybdenum (Mo), Tungsten (W);
   f) group VIII elements: Iron (Fe), Ruthenium (Ru), Cobalt (Co), Rhodium (Rh), Nickel (Ni), Palladium (Pd), Platinum (Pt), Iridium (Ir), Osmium (Os);
   g) oxides of the above metals;
   h) group II-VI compounds: ZnSe, ZnTe, CdS, CdTe, MgTe, ZnS;
   i) group III-V compounds: BN, GaAs, InAs, InSb, AlN, GaN, InN;
   j) group I-VII compounds: CuCl, CuBr, AgI;
   k) sphalerite structure compounds: $Ga_2Te_3$, $ZnSnP_2$, $ZnSnAs_2$;

l) Wurtzite structure compounds: SiC, MnS, MnSe, MnTe, $Al_2Se_3$;

m) group I, III, VI compounds: $CuGaTe_2$, $CuGaSe_2$, $CuLaS_2$;

n) group II, IV, V compounds: $ZnGeP_2$, $CdGeP_2$, $ZnGeAs_2$, $ZnSnAs_2$.

32. The method of claim 30 wherein the step of forming the metal clad segment on the portion of the waveguide body is performed by sputtering, vacuum deposition, plasma coating, brush coating, or spin coating of said metal.

33. The method of claim 30 further comprising matching the refractive indexes N1, N2, N3 and the refractive index N4 of the species of interest to control light leakage through the clad segment when the species of interest contacts the clad segment.

34. A method of forming a refractive index waveguide chemical sensor comprising
providing a waveguide body of refractive index N1;
forming a clad on the waveguide body, the clad having a thin film metal clad segment of metal or metal oxide or other metal compound or alloy on a portion of the waveguide body, the metal clad segment having a refractive index N3 and an effective thickness and light transmissivity which in combination with a surrounding medium produces a localized refractive index and a controlled leakage of light which modulates the transmission of light through the waveguide body as a function of the refractive index of the surrounding medium, the remainder of the clad having a refractive index N2 less than N1;
applying an over/underlayer of a second material on the metal clad segment, the metal clad segment having a strong affinity for a chemical species of interest, the second material having a suitable refractive index to produce controlled light leakage in the presence of the chemical species.

35. A method of forming a refractive index waveguide chemical sensor comprising;
providing a waveguide body of refractive index N1;
forming a clad on the waveguide body, the clad having a thin film metal clad segment of metal or metal oxide or other metal compound or alloy on a portion of the waveguide body, the metal clad segment having a refractive index N3 and an effective thickness and light transmissivity which in combination with a surrounding medium produces a localized refractive index and a controlled leakage of light which modulates the transmission of light through the waveguide body as a function of the refractive index of the surrounding medium, the remainder of the clad having a refractive index N2 less than N1;
applying a catalyst on the metal clad segment for reacting with a species of interest to form a reaction product, wherein the metal clad segment is specific to the reaction product.

36. Apparatus for detecting the presence of a particular chemical species, comprising:
at least one planar waveguide body, each planar waveguide body having at least one thin film metal clad segment on a waveguide body, each metal clad segment having a different sensitivity to various chemical species;
a light source operatively associated with each waveguide body to input a light signal into each waveguide body;
detection means operatively associated with each waveguide body to detect signals produced by modulation by each metal clad segment;
processing means for calculating information about one or more species from the detected signals produced by modulation by each metal clad segment.

37. The apparatus of claim 36 wherein each metal clad segment is formed on a separate waveguide body.

38. The apparatus of claim 36 comprising a plurality of metal clad segments all formed on a single waveguide body with the metal clad segments arranged in a pattern on the waveguide body.

39. The apparatus of claim 38 further comprising means for alternately flowing a sample over one of the metal clad segments while preventing flow over the other metal clad segments.

40. Apparatus for detecting the presence of a particular chemical species comprising:
a waveguide body having a pair of spaced parallel thin film metal clad segments on the waveguide body each metal clad segment having a different sensitivity to various chemical species;
a light source producing a pair of parallel light beams which propagate down the waveguide body, one beam in alignment with each of the metal clad segments, wherein each beam is affected by only one of the metal clad segments;
detection means operatively associated with the waveguide body to detect signals produced by modulation by each metal clad segment;
processing means for calculating information about one or more species from the detected signals produced by modulation by each metal clad segment.

41. Apparatus for detecting the presence of a particular chemical species, comprising:
a waveguide body having a pair o spaced parallel thin film metal clad segments, each metal clad segment having a different sensitivity to various chemical species;
a light source operatively associated with the waveguide body to input a light signal into the waveguide body;
detection means operatively associated with each waveguide body to detect signals produced by modulation by each metal clad segment;
alternate viewing means positioned between the waveguide body and detection means for alternately passing a light beam affected by one of the clad segments while blocking a light beam affected by the other clad segment;
processing means for calculating information about one or more species from the detected signals produced by modulation by each metal clad segment.

42. Apparatus for detecting the presence of a particular chemical species, comprising:
a waveguide body having a pair of metal clad segments, each metal clad segment having a different sensitivity to various chemical species and each of which affects light of a different wavelength,
a light source operatively associated with the waveguide body to input a light signal into the waveguide body;
detection means operatively associated with each waveguide body to detect signals produced by modulation by each metal clad segment;
processing means for calculating information about one or more species from the detected signals produced by modulation by each metal clad segment;

wherein the light source and detection means produce and detect light at the two wavelengths.

43. Apparatus for detecting the presence of a particular chemical species, comprising:

at least one wave guide body, each waveguide body having at least one thin film metal clad segment on a waveguide body, each metal clad segment having a different sensitivity to various chemical species;

a light source operatively associated with each waveguide body to input a light signal into each waveguide body;

detection means operatively associated with each waveguide body to detect signals produced by modulation by each metal clad segment;

processing means for calculating information about one or more species from the detected signals produced by modulation by each metal clad segment;

light blocking means positioned on at least one of the waveguide body and detection means for substantially blocking background light passing straight down the center of the waveguide body from reaching the detection means.

44. Apparatus for detecting the presence of a particular chemical species, comprising:

at least one waveguide body, each waveguide body having at least one thin film metal clad segment on a waveguide body, each metal clad segment having a different sensitivity to various chemical species;

a light source operatively associated with the waveguide body to input a light signal into the waveguide body;

detection means operatively associated with each waveguide body to detect signals produced by modulation by each metal clad segment;

processing means for calculating information about one or more species from the detected signals produced by modulation by each metal clad segment;

wherein the detection means includes means for detecting light passing through the metal clad segments.

* * * * *